(12) United States Patent
Hirai et al.

(10) Patent No.: US 11,000,302 B2
(45) Date of Patent: May 11, 2021

(54) GRASPING TREATMENT INSTRUMENT

(71) Applicant: OLYMPUS CORPORATION, Hachioji (JP)

(72) Inventors: Yuji Hirai, Sagamihara (JP); Takeshi Onaga, Koshigaya (JP)

(73) Assignee: OLYMPUS CORPORATION, Tokyo (JP)

( * ) Notice: Subject to any disclaimer, the term of this patent is extended or adjusted under 35 U.S.C. 154(b) by 91 days.

(21) Appl. No.: 16/198,319

(22) Filed: Nov. 21, 2018

(65) Prior Publication Data

US 2019/0090893 A1 Mar. 28, 2019

Related U.S. Application Data

(63) Continuation of application No. PCT/JP2016/067818, filed on Jun. 15, 2016.

(30) Foreign Application Priority Data

May 25, 2016 (WO) .................. PCT/JP2016/065455

(51) Int. Cl.
*A61B 17/28* (2006.01)
*A61B 17/29* (2006.01)
(Continued)

(52) U.S. Cl.
CPC .......... *A61B 17/2812* (2013.01); *A61B 17/29* (2013.01); *A61B 17/320092* (2013.01);
(Continued)

(58) Field of Classification Search
CPC ............ A61B 17/29; A61B 17/320092; A61B 2017/2926; A61B 2017/2932;
(Continued)

(56) References Cited

U.S. PATENT DOCUMENTS 5,662,667 A 9/1997 Knodel
6,214,023 B1 4/2001 Whipple et al.
(Continued)

FOREIGN PATENT DOCUMENTS

EP 0769273 A1 4/1997
EP 1177771 A1 2/2002
(Continued)

OTHER PUBLICATIONS

Sep. 20, 2016 International Search Report issued Patent Application No. PCT/JP2016/067818.
(Continued)

*Primary Examiner* — Katrina M Stransky
(74) *Attorney, Agent, or Firm* — Oliff PLC

(57) ABSTRACT

A grasping treatment instrument includes a sheath, a first grasping piece provided at a distal end of the sheath, a second grasping piece and a movable member. The second grasping piece is connected to the sheath at a first rotation axis perpendicular to a longitudinal axis of the sheath. The movable member is connected to the second grasping piece at the second rotation axis parallel to the first rotation axis, and is configured to move along the longitudinal axis. The first rotation axis is configured to move within the sheath or the second grasping piece in a plane perpendicular to the first rotation axis. The second rotation axis is configured to move within the movable member or the second grasping piece in a plane perpendicular to the second rotation axis.

14 Claims, 11 Drawing Sheets

(51) Int. Cl.
  *A61B 17/32*    (2006.01)
  *A61B 17/00*    (2006.01)
  *A61B 18/14*    (2006.01)
  *A61B 18/08*    (2006.01)

(52) U.S. Cl.
  CPC ........ *A61B 18/085* (2013.01); *A61B 18/1447* (2013.01); *A61B 2017/00526* (2013.01); *A61B 2017/2926* (2013.01); *A61B 2017/2932* (2013.01); *A61B 2017/2939* (2013.01); *A61B 2017/2947* (2013.01); *A61B 2017/320094* (2017.08)

(58) Field of Classification Search
  CPC .... A61B 2017/2939; A61B 2017/2947; A61B 2017/2933; A61B 17/2812; A61B 2017/2937; A61B 2017/2934; A61B 18/1447; A61B 18/085; A61B 2017/320094
  See application file for complete search history.

(56) References Cited

U.S. PATENT DOCUMENTS

| | | | |
|---|---|---|---|
| 6,325,811 | B1 | 12/2001 | Messerly |
| 2006/0079879 | A1* | 4/2006 | Faller ............. A61B 17/320092 606/40 |
| 2009/0088785 | A1 | 4/2009 | Masuda |
| 2010/0057117 | A1 | 3/2010 | Yamada |
| 2012/0116396 | A1* | 5/2012 | Price .................. A61B 18/1445 606/45 |
| 2012/0116433 | A1* | 5/2012 | Houser .............. A61B 17/2812 606/169 |
| 2016/0015419 | A1 | 1/2016 | Hibner et al. |
| 2016/0030076 | A1* | 2/2016 | Faller ............. A61B 17/320092 606/169 |
| 2016/0175001 | A1* | 6/2016 | Hibner ........... A61B 17/320092 606/28 |

FOREIGN PATENT DOCUMENTS

| | | |
|---|---|---|
| EP | 1698289 A2 | 9/2006 |
| EP | 1196098 B1 | 12/2008 |
| JP | H09-182757 A | 7/1997 |
| JP | 2001-187059 A | 7/2001 |
| JP | 2003-502102 A | 1/2003 |
| JP | 2003-510158 A | 3/2003 |
| JP | 2004-313540 A | 11/2004 |
| JP | 2009-82711 A | 4/2009 |
| JP | 2013-545535 A | 12/2013 |
| JP | 2014-518678 A | 8/2014 |

OTHER PUBLICATIONS

Aug. 16, 2016 International Search Report issued in Patent Application No. PCT/JP2016/065455.
Dec. 3, 2019 Office Action issued in Japanese Patent Application No. 2018-518865.
Dec. 3, 2019 Office Action issued in Japanese Patent Application No. 2018-518937.
Nov. 27, 2018 International Preliminary Report on Patentability issued in International Patent Application No. PCT/JP2016/065455.
Nov. 27, 2018 International Preliminary Report on Patentability issued in International Patent Application No. PCT/JP2016/067818.
U.S. Appl. No. 16/196,235, filed Nov. 20, 2018 in the name of Yuji Hirai et al.
Jan. 9, 2020 Search Report issued in European Patent Application No. 16903199.4.
Oct. 8, 2020 Office Action Issued in U.S. Appl. No. 16/196,235.
Aug. 24, 2020 Office Action issued in Chinese Patent Application No. 201680086015.1.
Aug. 25, 2020 Office Action issued in Chinese Patent Application No. 201680085992.X.
Jun. 23, 2020 Office Action issued in Japanese Patent Application No. 2018-518865.

* cited by examiner

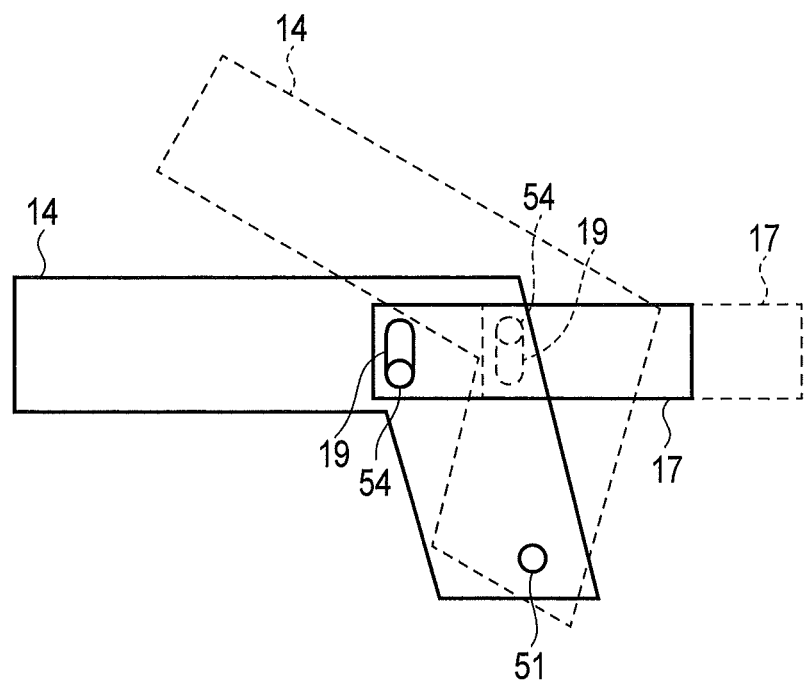
F I G. 5
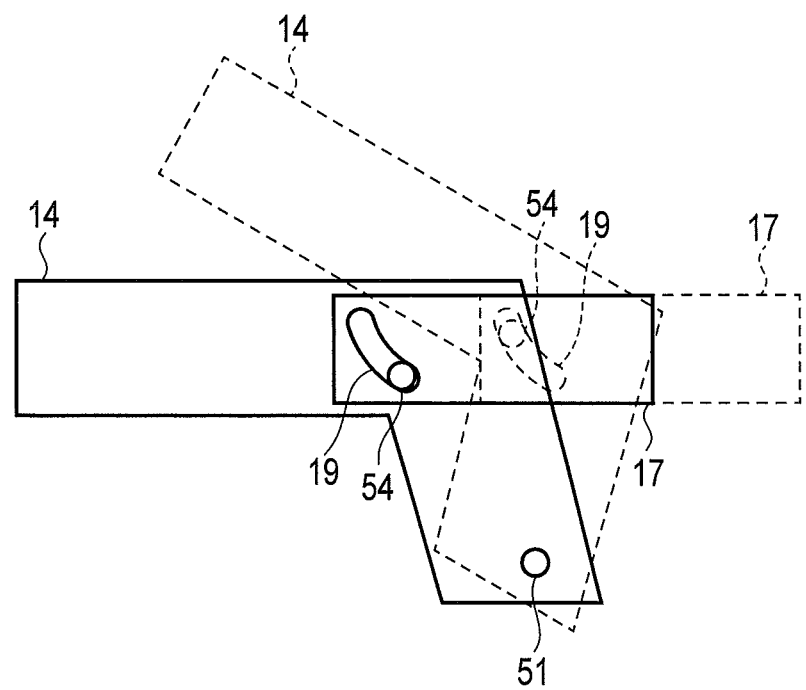
F I G. 6

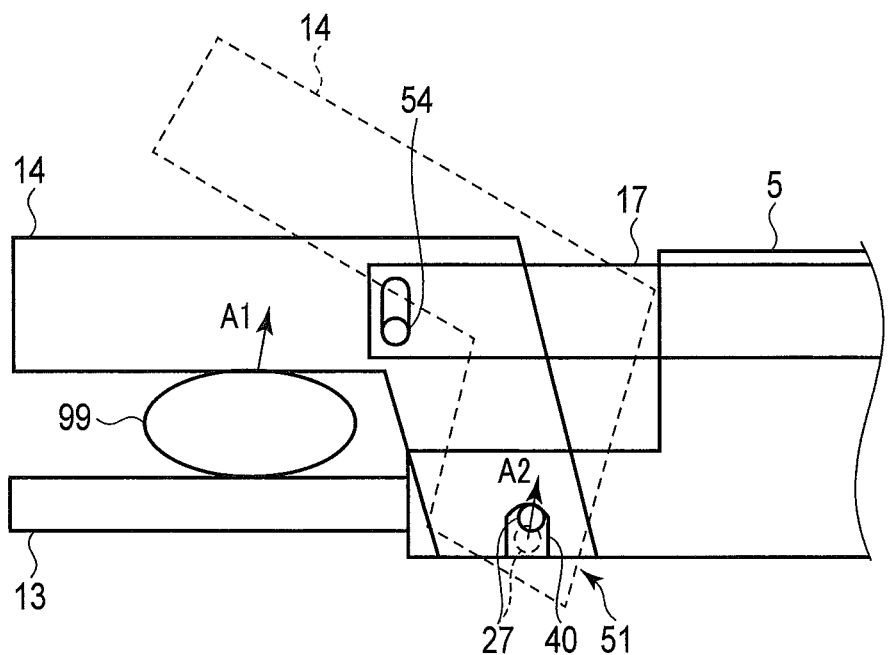
F I G. 7
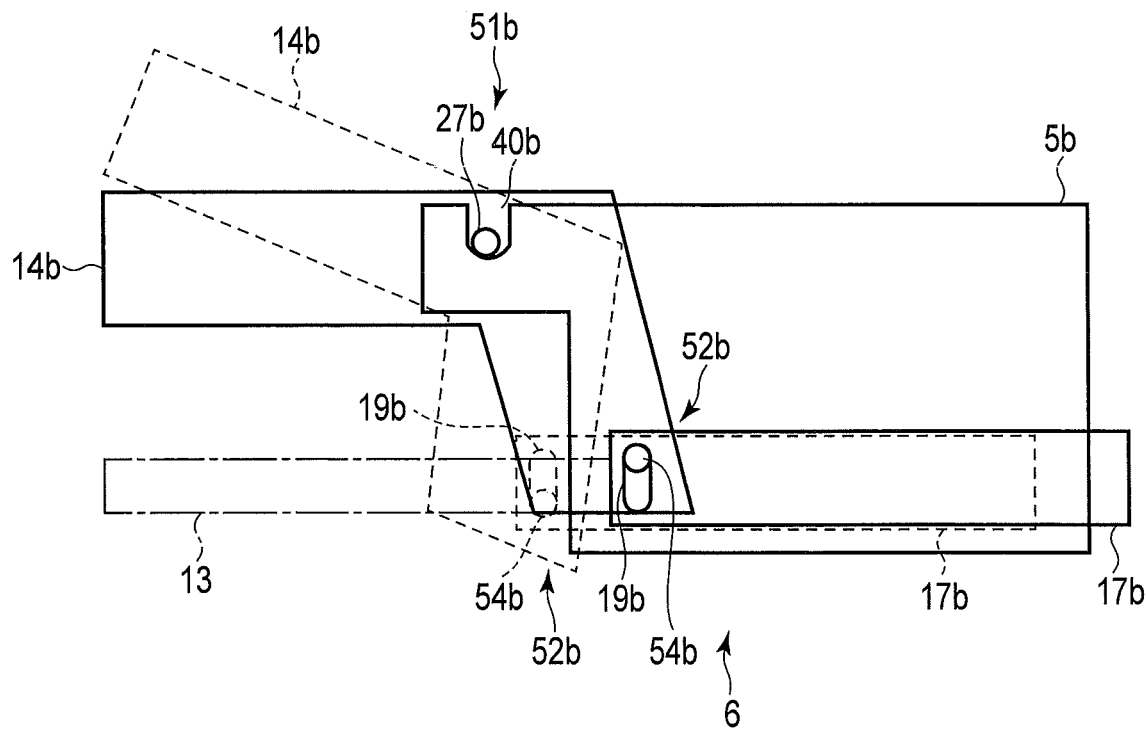
F I G. 8

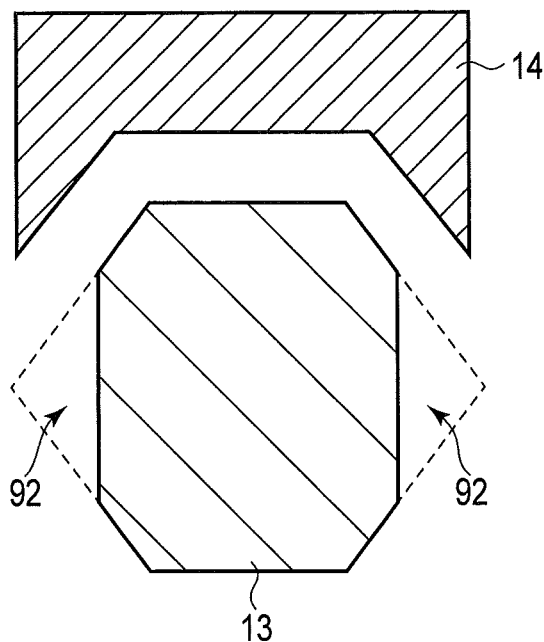
F I G. 14
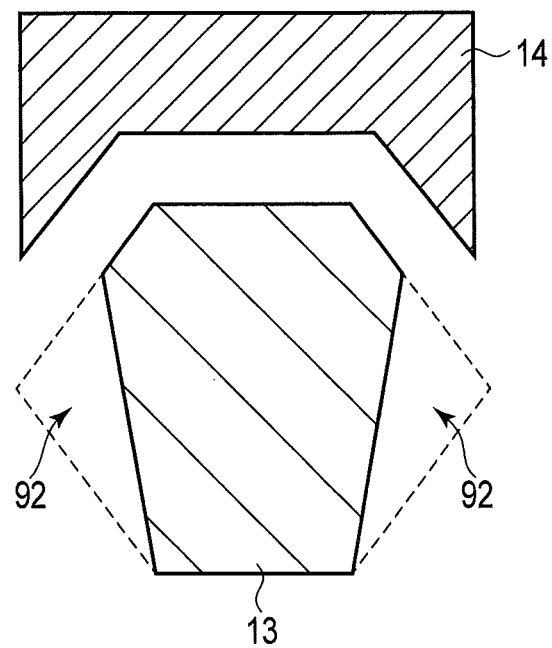
F I G. 15

GRASPING TREATMENT INSTRUMENT

CROSS-REFERENCE TO RELATED APPLICATIONS

This application is a Continuation Application of PCT Application No. PCT/JP2016/067818, filed Jun. 15, 2016, and based upon and claiming the benefit of priority from prior PCT Application No. PCT/JP2016/065455, filed May 25, 2016, the entire contents of all of which are incorporated herein by reference.

BACKGROUND OF THE INVENTION

1. Field of the Invention

The present invention relates to a grasping treatment instrument.

2. Description of the Related Art

A grasping treatment instrument for performing treatment by grasping a treatment target between a pair of grasping pieces is known. For example, such a grasping treatment instrument is disclosed in U.S. Patent Application Publication No. 2009/0088785 (Jpn. Pat. Appln. KOKAI Publication No. 2009-82711). In the grasping treatment instrument, at least one of a pair of grasping pieces is attached so as to rotate around an axis provided at a distal end portion of a sheath. The grasping piece rotates with respect to the sheath, whereby it is opened or closed with respect to the other grasping piece. Furthermore, the grasping piece attached so as to rotate is provided with a movable member at a position different from the aforementioned axis. The movable member, that is provided parallel to the sheath and movable along its longitudinal axis, is attached so that the grasping piece can rotate relative to the movable member.

In a grasping treatment instrument disclosed in U.S. Patent Application Publication No. 2009/0088785, a hole is provided in each of a sheath and a grasping piece, and by inserting a pin or the like into the holes, the grasping piece is attached so as to rotate with respect to the sheath. In addition, a hole is provided in each of the movable member and the grasping piece, and a pin or the like is inserted into the holes so that the grasping piece is attached so as to rotate with respect to the movable member.

BRIEF SUMMARY OF THE INVENTION

According to an aspect of the invention, a grasping treatment instrument includes a sheath; a first grasping piece provided at a distal end of the sheath; a second grasping piece connected to the sheath at a first rotation axis to rotate about the first rotation axis perpendicular to a longitudinal axis of the sheath so as to be opened and closed with respect to the first grasping piece; and a movable member connected to the second grasping piece at the second rotation axis parallel to the first rotation axis, configured to move along the longitudinal axis, and relatively rotating about the second rotation axis with respect to the second grasping piece so as to rotate the second grasping piece about the first rotation axis, wherein the first rotation axis is configured to move within at least one of the sheath and the second grasping piece in a plane perpendicular to the first rotation axis, and the second rotation axis is configured to move within at least one of the movable member and the second grasping piece in a plane perpendicular to the second rotation axis.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 is a view for explaining an outline of a relative movement between the second grasping member and the movable member;

FIG. 6 is a view for explaining an outline of a relative movement between the second grasping member and the movable member;

FIG. 7 is a view for explaining an outline of a relative movement between the second grasping member and the sheath;

FIG. 8 is a schematic view for explaining another configuration of the end effector;

FIG. 14 is a schematic cross-sectional view for explaining an example of a position of the depressed portion provided in the first grasping piece;

FIG. 15 is a schematic cross-sectional view for explaining an example of a position of the depressed portion provided in the first grasping piece;

DESCRIPTION OF EMBODIMENTS

An embodiment of the present invention will be described with reference to the drawings. The grasping treatment instrument according to the present embodiment is configured to grasp a living tissue to be treated, and apply energy to the tissue, thereby treating the tissue.

<Configuration of Grasping Treatment Instrument>

Figure 1:
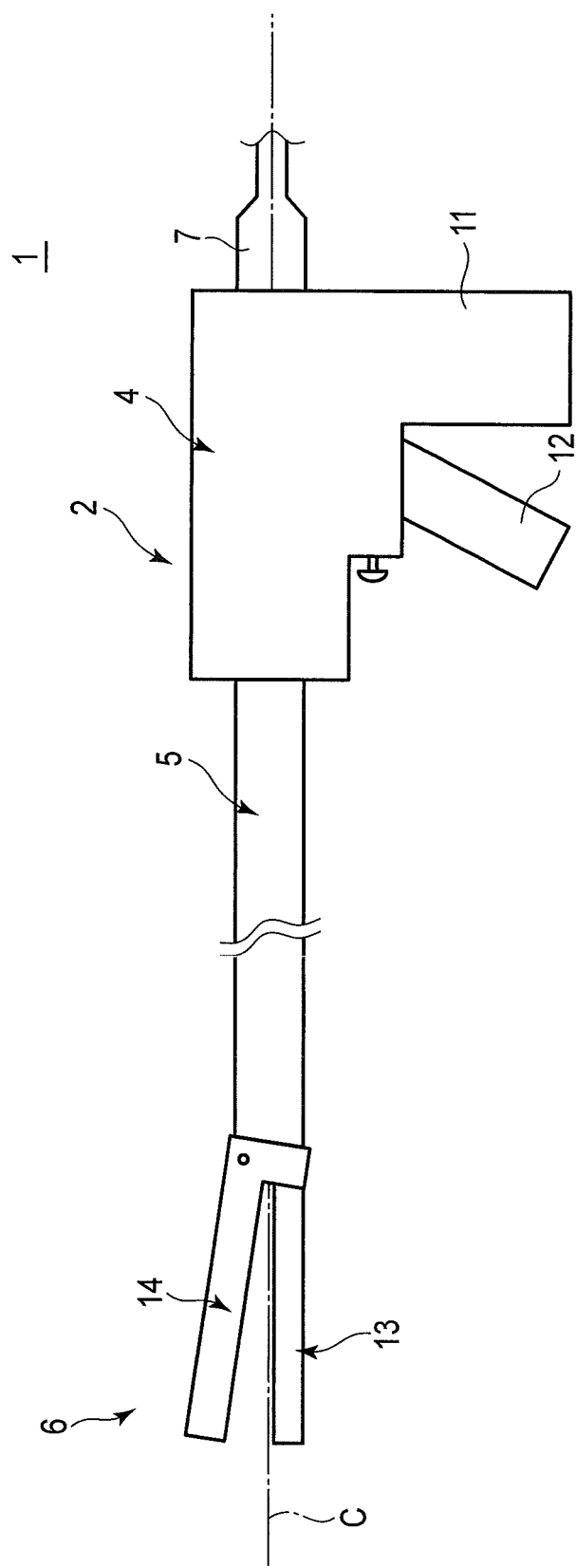
FIG. 1 is a view schematically showing a configuration example of a grasping treatment instrument according to one embodiment.

FIG. 1 schematically shows a configuration example of a grasping treatment instrument 1 according to the present embodiment. When a longitudinal axis C is defined, the grasping treatment instrument 1 includes an elongated cylindrical sheath 5 that extends along the longitudinal axis C. One end of the sheath 5 is provided with an operation unit 2, while the other end of the sheath 5 is provided with an end effector 6. The operation unit 2 is a portion grasped by the user to operate the grasping treatment instrument 1. The end effector 6 is configured to grasp the living tissue to be treated, and apply energy to the tissue. For explanation hereinafter, the end effector 6 side will be referred to as a distal side, and the operation unit 2 side will be referred to as a proximal side, along the longitudinal axis C.

The operation unit 2 includes a housing 4 to which the sheath 5 is connected. The housing 4 has an appropriate length along the longitudinal axis C. A grip 11 extends from a portion at the proximal side of the housing 4 in a direction away from the longitudinal axis C. The grip 11 is fixed to the housing 4, and functions as a fixed handle. A handle 12 extends from a portion at the distal side of the grip 11 of the housing 4 within the same plane as the plane on which the grip 11 is provided. The handle 12 is attached to the housing 4 to rotate about a support axis provided in the housing 4 so that the distance from the grip 11 changes. The handle 12 functions as a movable handle.

The user grasps the grip 11 and the handle 12 so that the grip 11 and the handle 12 are opened or closed, and performs an operation to change the distance between the grip 11 and the handle 12. The end effector 6 operates in conjunction with this operation.

The positional relationship between the grip 11 and the handle 12 is not limited to the example shown in FIG. 1. For example, the handle serving as the movable handle may be disposed at the proximal side relative to the grip serving as the fixed handle. Moreover, the grip as the fixed handle and the handle as the movable handle may extend along the longitudinal axis C in which the handle is displaced to change the distance between the handle and the longitudinal axis C.

Returning to the example shown in FIG. 1, the explanation will be continued. One end of a cable 7 is connected to the proximal side of the housing 4. The other end of the cable 7 is connected to a power supply device (not shown). The cable 7 is a cable for receiving, from the power supply device, energy supplied to the end effector 6.

The end effector 6 includes a first grasping piece 13, and a second grasping piece 14. In the present embodiment, the first grasping piece 13 is arranged to be fixed along the longitudinal axis C. The second grasping piece 14 is provided to face the first grasping piece 13. The second grasping piece 14 is connected to the sheath 5 to be opened/closed with respect to the first grasping piece 13. The grasping treatment instrument 1 is configured so that the second grasping piece 14 is opened/closed in conjunction with the displacement of the handle 12.

For the sake of explanation, a direction in which the second grasping piece 14 is opened/closed is defined as a vertical direction, and the side on which the second grasping piece 14 is provided will be referred to as a upper side, while the side on which the first grasping piece 13 is provided will be referred to as a lower side. In addition, based on the vertical direction, a right side and a left side viewed from the proximal side to the distal side are defined. That is, in FIG. 1, the back side on the paper will be referred to as a right side while the front side will be referred to as a left side. In the following description, for each member, a side closer to the center axis of the sheath 5 will be referred to as an inner side while a side far from the center axis will be referred to as an outer side.

Figure 2:
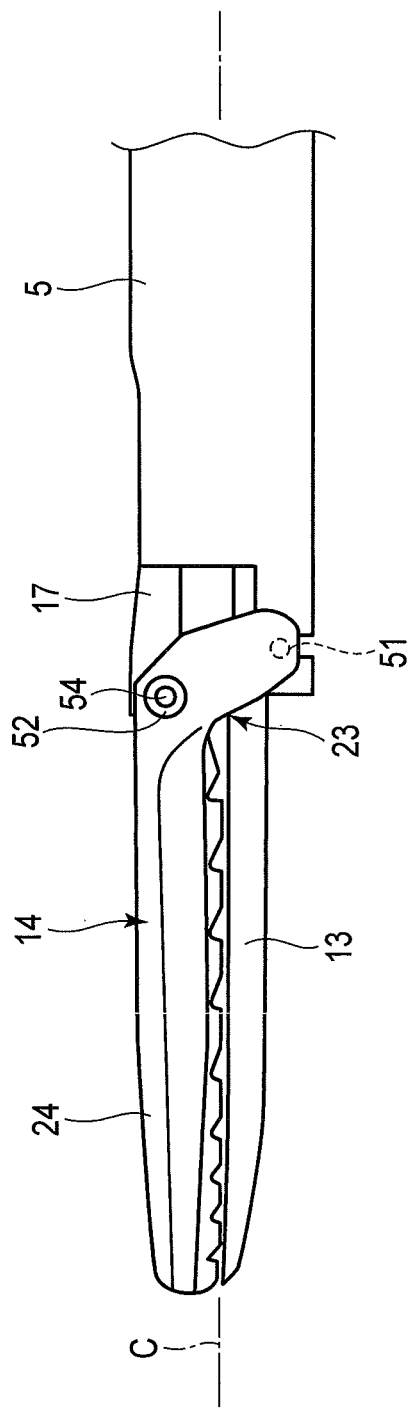
FIG. 2 is a plan view schematically showing a configuration example of an end effector.

FIG. 2 shows a configuration example of the end effector 6. As described above, the sheath 5 and the first grasping piece 13 extend along the longitudinal axis C, and they are fixed. The second grasping piece 14 includes a grasping piece main body 24 that is a part facing the first grasping piece 13, and a projecting piece 23, that extends from the grasping piece main body 24 to the lower side, i.e., to the first grasping piece 13 side. A first rotation axis 51 is provided at the lower part of the projecting piece 23. A second rotation axis 52 including an axis member 54 is provided at the upper part of the projecting piece 23. The first rotation axis 51 and the second rotation axis 52 are provided in a direction perpendicular to the plane including the longitudinal axis C and the axis indicating the vertical direction. In addition, the first rotation axis 51 and the second rotation axis 52 are provided on sides opposite to each other with the central axis of the sheath 5 therebetween. The first rotation axis 51 is an axis to support the second grasping piece 14 in a rotatable manner with respect to the sheath 5.

A movable member 17 having an elongated shape is provided in the sheath 5 in parallel to the longitudinal axis C. A distal side of the movable member 17 is connected to the second grasping piece 14 via the second rotation axis 52. In other words, the second rotation axis 52 is an axis to support the movable member 17 and the second grasping piece 14 in a relatively rotatable manner.

A proximal side of the movable member 17 extends to the operation unit 2. In conjunction with the movement of the handle 12, the movable member 17 is configured to move to the distal side or the proximal side in parallel with the longitudinal axis C inside the sheath 5. When the handle 12 is displaced to the grip 11 side, i.e. the proximal side, the movable member 17 is displaced to the distal side. When the handle 12 moves away from the grip 11, i.e. the distal side, the movable member 17 moves to the proximal side.

When the movable member 17 moves to the proximal side, the second rotation axis 52 moves to the proximal side, and the upper part of the projecting piece 23 is pulled toward the proximal side. As a result, the grasping piece main body 24 moves in a manner that the distal end thereof moves upward so that the grasping piece main body 24 is opened with respect to the first grasping piece 13. When the movable member 17 is displaced to the distal side, the second rotation axis 52 is displaced to the distal side, and the upper part of the projecting piece 23 is pushed toward the distal side. As a result, the grasping piece main body 24 moves in a manner that the distal end thereof moves downward so that the grasping piece main body 24 is closed with respect to the first grasping piece 13.

Figure 3:
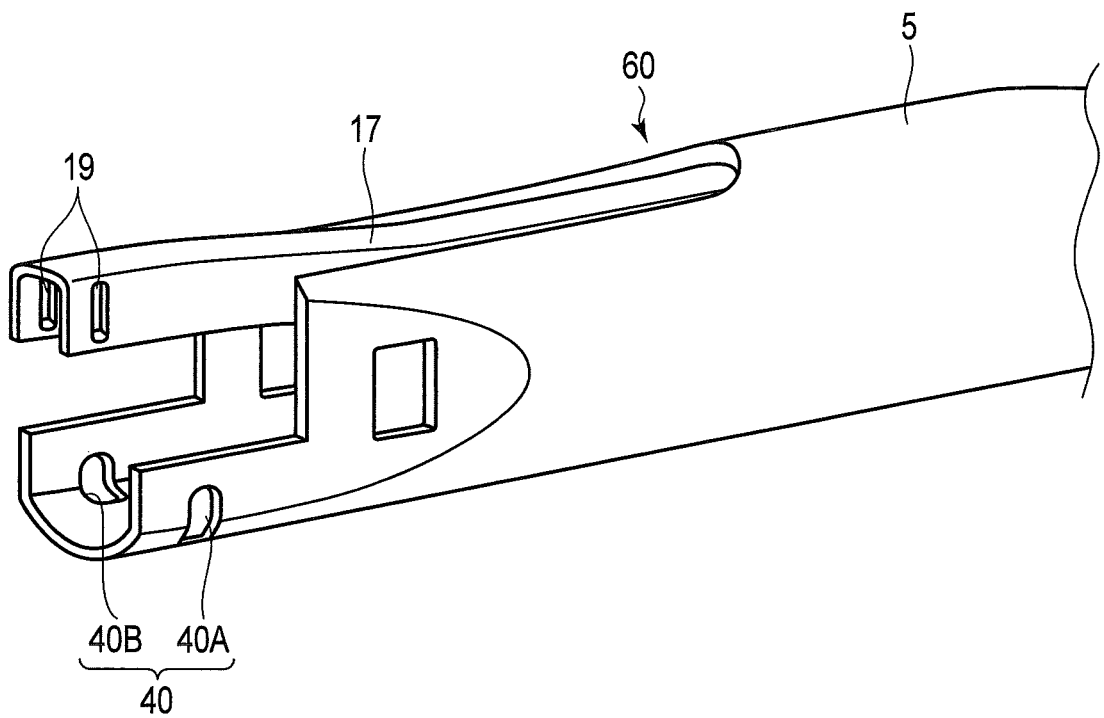
FIG. 3 is a perspective view schematically showing a configuration example of a sheath and a movable member.
Figure 4:
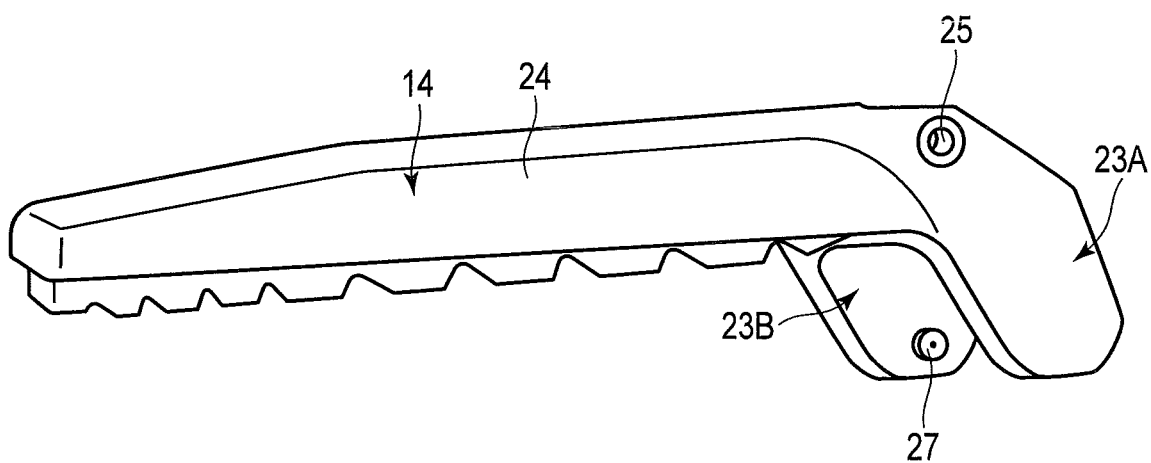
FIG. 4 is a perspective view schematically showing a configuration example of a second grasping member.

FIG. 3 is a perspective view showing the structures of the sheath 5 and the movable member 17. FIG. 4 is a perspective view showing the structure of the second grasping piece 14.

As shown in FIG. 3, the distal end portion of the sheath 5 has a shape in which the upper part is cut off. Thus, the cross section perpendicular to the longitudinal axis C of the distal end portion of the sheath 5 is U-shaped having a bottom surface on the lower side. At the distal end part of the sheath 5, a notch is formed from the left side surface to the bottom surface. This notch will be referred to as a left notch 40A. Similarly, at the distal end part of the sheath 5, a notch is formed from the right side surface to the bottom surface. This notch will be referred to as a right notch 40B. The left notch 40A and the right notch 40B are symmetrical. The left notch 40A and the right notch 40B will be collectively referred to as sheath notches 40. The sheath notches 40 serve as a bearing of the first rotation axis 51. Thus, the upper side of each of the sheath notches 40 is cut into a circular shape to hold the axis.

As shown in FIG. 4, the projecting piece 23 on the left of the second grasping piece 14 will be referred to as a left projecting piece 23A, while the projecting piece 23 on the right of the second grasping piece 14 will be referred to as a right protruding piece 23B. The inner surface of the left projecting piece 23A and the inner surface of the right projecting piece 23B are provided with cylindrical protrusions which are symmetrical to each other. The protrusions will be referred to as grasping piece protrusions 27. The grasping piece protrusions 27 function as an axis member serving as an axis of the first rotation axis 51. The center axis of the cylindrical grasping piece protrusions 27 extends in a right-left direction. The grasping piece protrusions 27 of the second grasping piece 14 are fitted into the sheath notches 40 of the sheath 5.

As shown in FIG. 3, at the distal end portion of the movable member 17, axis holes 19 are formed so as to penetrate the movable member 17 in the right-left direction. The axis holes 19 are holes through which the axis member 54 of the second rotation axis 52 passes. The width of the axis holes 19, viewed from the right-left direction, is approximately equal to the outer diameter of the axis member 54, but the vertical length of the axis holes 19 is longer than the outer diameter of the axis member 54. That is, the axis member 54 passing through the axis holes 19 can rotate within the axis holes 19, and can make parallel movements in the vertical direction.

The movable member 17 is curved upward at its distal side, and the upper surface of the movable member 17 is located above the upper surface of the sheath 5. A notch 60 is provided on the upper side of the sheath 5 so that the movable member 17 is not brought into contact with the sheath 5 when moved to the proximal side. Since the movable member 17 is curved upward, the second rotation axis 52 can be provided on a further upper side, and the distance between the first rotation axis 51 and the second rotation axis 52 becomes longer as compared to when the movable member 17 is not curved. As will be described later, the second grasping piece 14 moves with the first rotation axis 51 as a fulcrum, and an input force is applied to the second rotation axis 52. The increase in the distance between the first rotation axis 51 and the second rotation axis 52 results in an increase in a leverage ratio.

As shown in FIG. 4, the upper part of the projecting piece 23 of the second grasping piece 14 is provided with grasping piece holes 25, which are holes through which the axis member 54 of the second rotation axis 52 passes.

At the time of assembling the second grasping piece 14, the sheath 5, and the movable member 17, the grasping piece protrusions 27 of the second grasping piece 14 are fitted into the sheath notches 40 from the lower side of the sheath 5. Subsequently, the axis member 54 of the second rotation axis 52 is inserted to penetrate the grasping piece holes 25 of the second grasping piece 14 and the axis holes 19 of the movable member 17. The axis member 54 is fixed to the grasping piece holes 25 of the second grasping piece 14.

As described above, in the present embodiment, the first rotation axis 51 and the second rotation axis 52 are provided to be parallel.

The configurations of the first grasping piece 13 and the second grasping piece 14 may be appropriately changed according to functions of the grasping treatment instrument 1. The grasping treatment instrument 1 according to the present embodiment may apply any energy to the living tissue. For example, the grasping treatment instrument 1 may be a high-frequency treatment instrument allowing a high-frequency current to flow in a living tissue. In this case, electrodes are provided on the surfaces of the first grasping piece 13 and the second grasping piece 14 that are brought into contact with the living tissue. The grasping treatment instrument 1 as described above allows the high-frequency current to flow in a living tissue grasped using the electrodes, thereby treating the living tissue. The grasping treatment instrument 1 may be an ultrasonic treatment instrument. In an example of this case, the first grasping piece 13 passes through the sheath 5, and reaches the housing 4 of the operation unit 2. In the housing 4, an ultrasonic transducer is provided, and vibration generated by the ultrasonic transducer is transmitted to the first grasping piece 13 to thereby vibrate the first grasping piece 13. Using this vibration, the grasping treatment instrument 1 treats the grasped living tissue of the treatment target. Furthermore, a heater may be provided in the first grasping piece 13 or in the second grasping piece 14. Heat generated by the heater is transmitted to the living tissue. Using this heat, the grasping treatment instrument 1 treats the living tissue. For the grasping treatment instrument 1, a combination of the above-described energies may be used. That is, the grasping treatment instrument 1 may, for example, be a treatment instrument that allows a high-frequency current to flow in a living tissue while ultrasonically vibrating the first grasping piece 13.

<Opening/Closing Operation of End Effector>

A further description will be given of the opening/closing operation of the second grasping piece 14 of the end effector 6 according to the present embodiment. FIG. 5 shows a schematic diagram of the movable member 17 and the second grasping piece 14. In FIG. 5, a dashed line schematically shows an open state in which the second grasping piece 14 is opened with respect to the first grasping piece 13, and a solid line schematically shows a closed state in which the second grasping piece 14 is closed with respect to the first grasping piece 13.

If the first rotation axis 51 fixed to the sheath 5 does not move, the second grasping piece 14 rotates about the first rotation axis 51. Along with the operation of the handle 12 of the operation unit 2, the movable member 17 moves in the longitudinal axis direction thereof. In FIG. 5, in the open state indicated by the dashed line, the movable member 17 is positioned on the proximal side, whereas in the closed state indicated by the solid line, the movable member 17 is positioned on the distal side. When a state is changed from the open state indicated by the dashed line to the closed state indicated by the solid line, that is, when the movable member 17 moves from the proximal side to the distal side, the movable member 17 applies force to the axis member 54. That is, the movable member 17 pushes the axis member 54 toward the distal side. As a result, the second grasping piece 14, to which the axis member 54 is fixed, rotates about the first rotation axis 51, and the open state changes to the closed state. Since this motion is a rotational motion about the first rotation axis 51, the position of the axis member 54 changes in the vertical direction as shown in FIG. 5. In the present embodiment, since the axis holes 19 provided in the movable member 17 through which the axis member 54 passes are long in the vertical direction, the axis member 54 moves upward and downward while rotating in the axis holes 19.

Suppose that the axis holes 19, through which the axis member 54 passes, are circular holes which coincide with the diameter of the axis member 54. In this case, the movable member 17 is deflected upward/downward as the axis member 54 is displaced in the vertical direction when the second grasping piece 14 is opened/closed. If the movable member 17 is deflected upward/downward, the movable member 17 cannot efficiently transmit to the second grasping piece 14 the force accompanying the displacement to the distal side or the proximal side. In other words, since the axis holes 19 provided in the movable member 17 are longer in the vertical direction than the thickness of the axis member 54, the movable member 17 can efficiently transmit the force to the second grasping piece 14.

In the above-described embodiment, the axis holes 19, that allow movement of the axis member 54 provided in the movable member 17, have a shape in which the axis member 54 can move in a direction perpendicular to the longitudinal axis C and can linearly move in the vertical direction. However, the present invention is not limited to this structure. As shown in FIG. 6, the axis holes 19 in which the axis member 54 can move may have a curved shape. In particular, the preferable shape of the axis holes 19 is that the line perpendicular to the contact surface of the axis member 54 always coincides with the perpendicular line to the line connecting the first rotation axis 51 and the axis member 54. With this shape, the direction of the force transmitted from the movable member 17 to the axis member 54 always coincides with the direction of the perpendicular line to the line connecting the first rotation axis 51 and the axis member 54, that is, the moving direction of the axis member 54. For this reason, the movable member 17 efficiently applies the force to the axis member 54, that is, the second grasping piece 14. As described above, it is preferable that a locus of the second rotation axis 52 depicted on the movable member 17 in the process of transition from the open state to the closed state has a shape in which the line perpendicular to the tangent of the locus in the process of the above transition always coincides with the line perpendicular to the line connecting the first rotation axis 51 and the second rotation axis 52.

Next, the behavior of the first rotation axis 51 in the opening/closing operation of the second grasping piece 14 will be described with reference to FIG. 7. As described above, the first rotation axis 51 includes the grasping piece protrusions 27 provided on the second grasping piece 14, and the sheath notches 40 provided on the sheath 5. As shown in FIG. 7, the sheath notches 40 are larger than the grasping piece protrusions 27, and thus the grasping piece protrusions 27 can move in the sheath notches 40. On the other hand, as shown in FIG. 7, when a treatment target 99 is grasped between the first grasping piece 13 and the second grasping piece 14, the movable member 17 moves to the distal side. At this time, the second grasping piece 14 rotates in the closing direction about the grasping piece protrusions 27 forming the first rotation axis 51. The direction of the force applied to the grasping piece protrusions 27 at this time is an upper direction at the proximal side. An upward force as indicated by an arrow A1 from the treatment target 99 is applied to the second grasping piece 14. By this action, the upward force is applied to the grasping piece protrusions 27. Therefore, as shown by an arrow A2, the upward and slightly proximal-directional force is applied to the grasping piece protrusions 27. Therefore, the grasping piece protrusions 27 are supported by the sheath notches 40 of the sheath 5.

In this way, when a state in which the second grasping piece 14 is most opened with respect to the first grasping piece 13 is defined as an open state, and a state in which the second grasping piece 14 is most closed with respect to the first grasping piece 13 is defined as a closed state, in the process of transition from the open state to the closed state, the grasping piece protrusions 27 are supported by the sheath notches 40 in the process of transition from a predetermined state to the closed state. During this period, the first rotation axis 51 is not displaced to the sheath 5 and the second grasping piece 14 in a plane perpendicular to the first rotation axis 51. In this manner, the grasping piece protrusions 27 do not come out from the sheath notches 40.

In the grasping treatment instrument 1 according to the present embodiment, the axis holes 19 of the movable member 17 hold the axis member 54 fixed to the second grasping piece 14. The axis holes 19 are longer than the outer diameter of the axis member 54 so that the axis member can rotate and move within a plane perpendicular to the second rotation axis 52. As a result, the second rotation axis 52 moves within the movable member 17 in the plane perpendicular to the second rotation axis 52. The moving direction is a direction intersecting with the longitudinal axis C on which the movable member 17 moves. As a result, the movable member 17 is not deflected in the process where the second grasping piece 14 moves from the open state to the closed state. This improves the transmission efficiency of the force from the movable member 17 to the second grasping piece 14, as compared to when the movable member 17 is deflected. When the living tissue is treated by the end effector 6, if the grasping force by the first grasping piece 13 and the second grasping piece 14 is higher, the treatment efficiency increases. Therefore, the improvement in the transmission efficiency of the force from the movable member 17 to the second grasping piece 14 can improve the treatment efficiency of the living tissue by the end effector 6.

Furthermore, in the grasping treatment instrument 1 according to the present embodiment, the sheath notches 40 provided in the sheath 5 hold the grasping piece protrusions 27 provided in the second grasping piece 14. The sheath notches 40 include holes larger than the outer diameter of the grasping piece protrusions 27 so that the grasping piece protrusions 27 can rotate and move in a plane perpendicular to the first rotation axis 51. Thus, the first rotation axis 51 can move within the range of the sheath notches 40. As a result, the degree of freedom of the position of the second grasping piece 14 with respect to the position of the movable member 17 is improved. Thus, when the living tissue is grasped between the first grasping piece 13 and the second grasping piece 14, the angle at which the second grasping piece 14 is brought into contact with the living tissue can be adjusted. The living tissue grasped by the first grasping piece 13 and the second grasping piece 14 differs in the size, etc. depending on the treatment target. Since there is a certain degree of freedom of the position of the second grasping piece 14, it is possible to appropriately grasp a living tissue by the first grasping piece 13 and the second grasping piece 14 regardless of the size, etc. of the living tissue. As a result, the treatment efficiency of the living tissue by the end effector 6 is improved.

In addition, the sheath notches 40 each include an opening on the lower side. That is, the outer edge of each of the sheath notches 40, as holes for holding the grasping piece protrusions 27, includes an opening. Therefore, at the time of assembling the end effector 6, the grasping piece protrusions 27 of the second grasping piece 14 can be easily inserted from the opening on each of the lower sides of the sheath notches 40. Therefore, the assembling efficiency of the end effector 6 is improved as compared to when such an opening is not provided.

Although the outer edge of the axis hole 19 provided in the movable member 17 is closed, it may be partially opened like the sheath notch 40 provided in the sheath 5. However, when the outer edge of the axis hole 19 provided in the movable member 17 is closed, the strength of the movable member 17 becomes higher than when it is opened, and thus the outer edge of the axis hole 19 is preferably closed.

On the other hand, the axis hole 19 provided in the movable member 17 may be partially opened, and the outer edge of the sheath notch 40 provided in the sheath 5 may be closed. In this case, at the time of assembly, the axis member of the second grasping piece 14 is fitted into the open axis holes 19 of the movable member 17, and then the axis member of the second grasping piece 14 is put through and fixed to the sheath notches 40 of the sheath 5.

Modification

<Regarding Second Rotation Axis>

According to the above-described embodiment, in the second rotation axis 52, the axis member 54 penetrates the axis holes 19 of the movable member 17. However, the present invention is not limited to this structure. For example, the present invention may employ a structure in which a boss is provided instead of the axis member 54 on the second grasping piece 14. Grooves that hold the boss are provided in the movable member 17 as grooves corresponding to the axis holes 19.

Furthermore, in the above-described embodiment, the second rotation axis 52 moves within the movable member 17 in a plane perpendicular to the second rotation axis 52. Similarly, the second rotation axis 52 may move within the second grasping piece 14 in a plane perpendicular to the second rotation axis 52. That is, the present invention may employ a structure in which an axis member or boss of the second rotation axis 52 is fixed to the movable member 17, and the second grasping piece 14 is provided with holes or grooves where the axis member or boss can rotate and move. Furthermore, the second grasping piece 14 may be configured in such a manner that as the axis member moves in the axis holes provided in the movable member 17 and the axis holes provided in the second grasping piece 14, the second rotation axis 52 moves within the movable member 17 and the second grasping piece 14.

<Regarding First Rotation Axis>

According to the above-described embodiment, in the first rotation axis 51, the sheath notches 40 shown in FIG. 3 are holes penetrating the sheath 5. However, the present invention is not limited to this structure. For example, the sheath notches 40 may be grooves that hold the grasping piece protrusions 27. In the example shown in FIG. 3, the left notch 40A and the right notch 40B of the sheath notches 40 are separated, but they may be connected. In this case, instead of the grasping piece protrusions 27, a shaft connecting the grasping piece protrusions 27 may be provided on the second grasping piece 14. However, in this case, the strength of the sheath 5 might be lower than that of the structure shown in FIG. 3.

In the above-described embodiment, the first rotation axis 51 moves within the sheath 5 in a plane perpendicular to the first rotation axis 51. Similarly, the first rotation axis 51 may move within the second grasping piece 14 in a plane perpendicular to the first rotation axis 51. That is, the present invention may employ a structure in which the axis member or boss of the first rotation axis 51 is fixed to the sheath 5, and the second grasping piece 14 is provided with holes or grooves in which the axis member or boss can rotate and move. Furthermore, the present invention may employ a structure in which as the axis member moves in the axis holes provided in the sheath 5 and the axis holes provided in the second grasping piece 14, the first rotation axis 51 moves within the sheath 5 and the second grasping piece 14.

<Regarding Other Configurations of End Effector>

The configuration of the end effector 6 is not limited to the above-described embodiment. For example, the configuration shown in the schematic diagram of FIG. 8 may be adopted. That is, in the example shown in FIG. 8, a second grasping piece 14b is opened and closed with respect to the first grasping piece 13 fixed to a sheath 5b. In FIG. 8, a solid line indicates a closed state in which the second grasping piece 14b is closed, and a dashed line indicates an open state in which the second grasping piece 14b is opened.

A rotation axis of the second grasping piece 14b when the second grasping piece 14b is opened/closed is referred to as a first rotation axis 51b. At this time, the first rotation axis 51b is provided on an upper side of the second grasping piece 14b. Furthermore, a second rotation axis 52b is provided on a lower side of the second grasping piece 14b. A movable member 17b is connected to the second grasping piece 14b via the second rotation axis 52b.

In the first rotation axis 51b, for example, grasping piece protrusions 27b are provided on the second grasping piece 14b. The sheath 5b is provided with sheath notches 40b each having an opening on the upper side. In the second rotation axis 52b, an axis member 54b is provided on the second grasping piece 14b, and elongated axis holes 19b are provided in the movable member 17b so that the axis member 54b penetrates it.

In the example shown in FIG. 8 as well, the first rotation axis 51b and the second rotation axis 52b can move in a plane perpendicular to their axes. As a result, the function and effect similar to those according to the above-described embodiment can be obtained.

[Regarding Configuration of Handle]

<Regarding Position of Support Axis of Handle>

Figure 9:
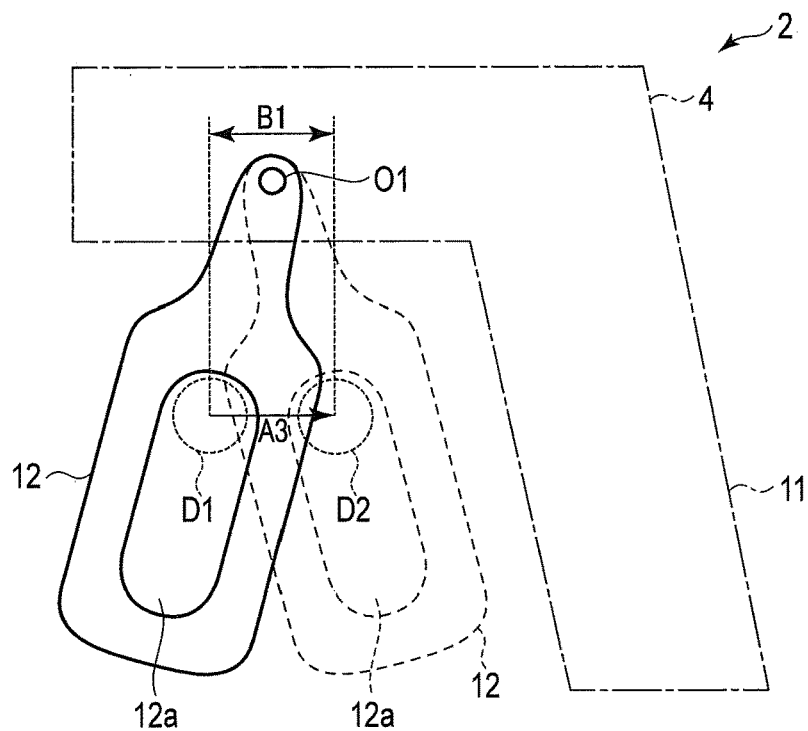
FIG. 9 is a view for explaining an example of a position of a support axis of a handle.
Figure 10:
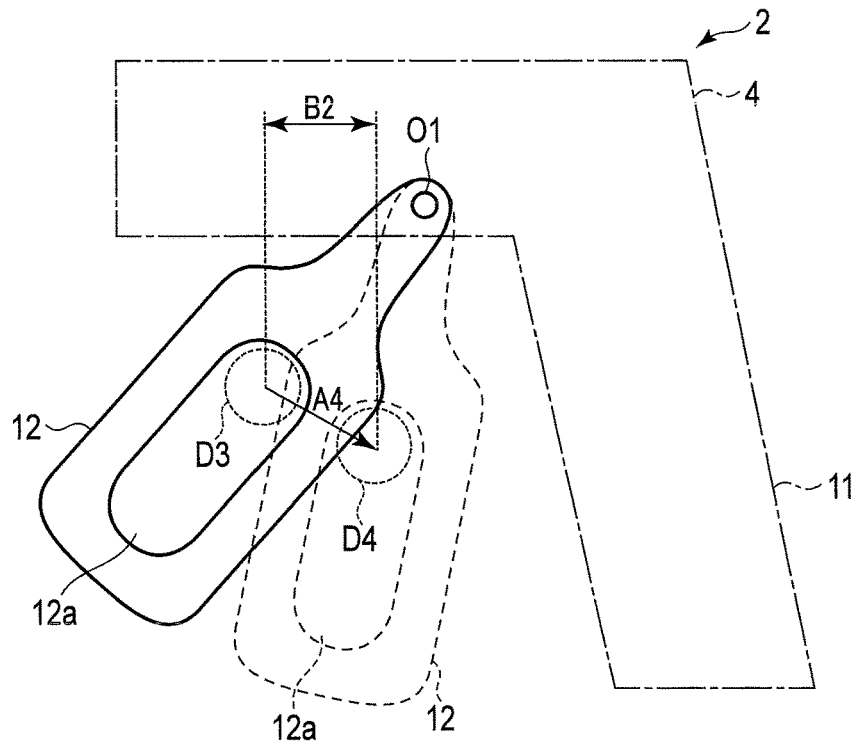
FIG. 10 is a view for explaining an example of a position of the support axis of the handle.

The configuration of the handle 12 of the operation unit 2 will be described with reference to FIG. 9 and FIG. 10. The handle 12 is attached so as to rotate about a support axis O1 provided in the housing 4 of the operation unit 2. Attention will be focused on the positional relationship between a movable range of the handle 12 and the support axis O1. In FIG. 9 and FIG. 10, the handle 12 drawn by a solid line shows an open state in which the handle 12 is positioned on the most distal side, while the handle 12 drawn by a dashed line shows a closed state in which the handle 12 is displaced to the most proximal side. The user's fingers operating the handle 12 are inserted into a hole 12a provided in the handle 12.

In the example shown in FIG. 9, when the handle 12 is displaced from the open state to the closed state, the user's fingers move from position D1 to position D2. On the other hand, in the example shown in FIG. 10, when the handle 12 is displaced from the open state to the closed state, the user's fingers move from position D3 to position D4. In the example shown in FIG. 9, the movement of the user's fingers is directed to the grip 11 as indicated by an arrow A3, and the user can easily apply the grasping force to the handle 12. On the other hand, in the example shown in FIG. 10, the movement of the user's finger is not directed to the grip 11 as indicated by an arrow A4, and the user cannot easily apply the grasping force to the handle 12. For this reason, the example shown in FIG. 9 is preferable to the example shown in FIG. 10.

That is, it is preferable as shown in FIG. 9 that the support axis O1 of the handle 12 be located inside the range B1 between the lines extending upward from the positions D1 and D2. In the example shown in FIG. 10, the support axis O1 of the handle 12 is not located inside the range B2 between the lines extending upward from the positions D3 and D4.

<Regarding Spring Provided in Handle>

Figure 11:
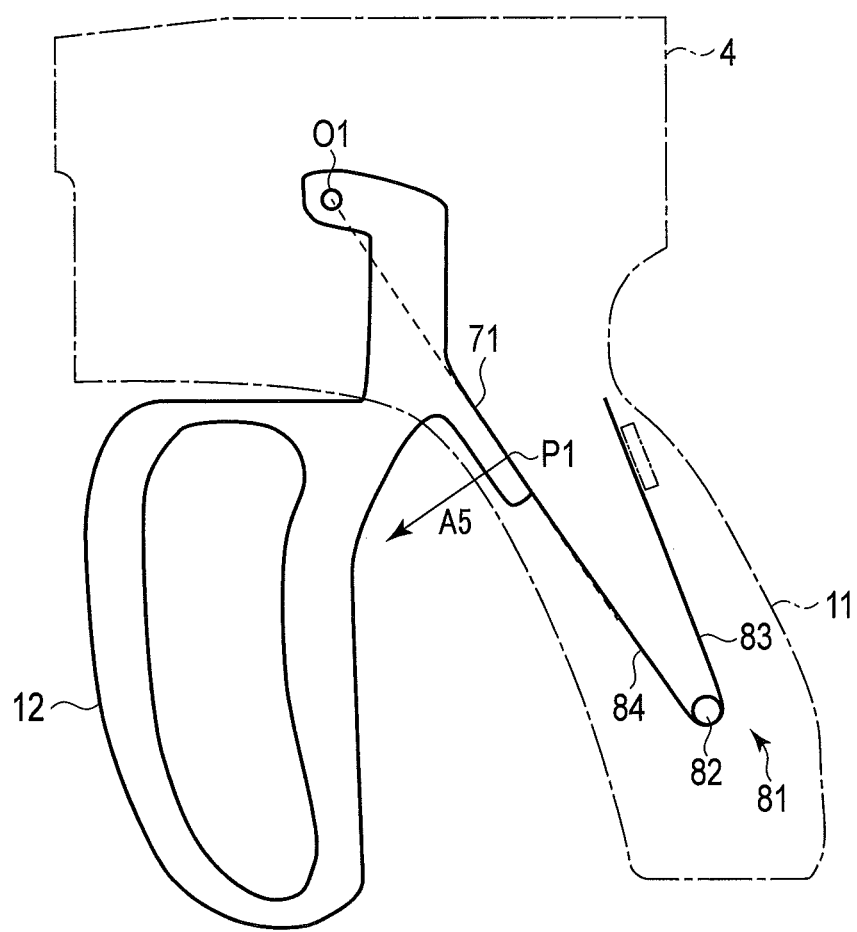
FIG. 11 is a view for explaining a configuration example of a spring provided in the handle.
Figure 12:
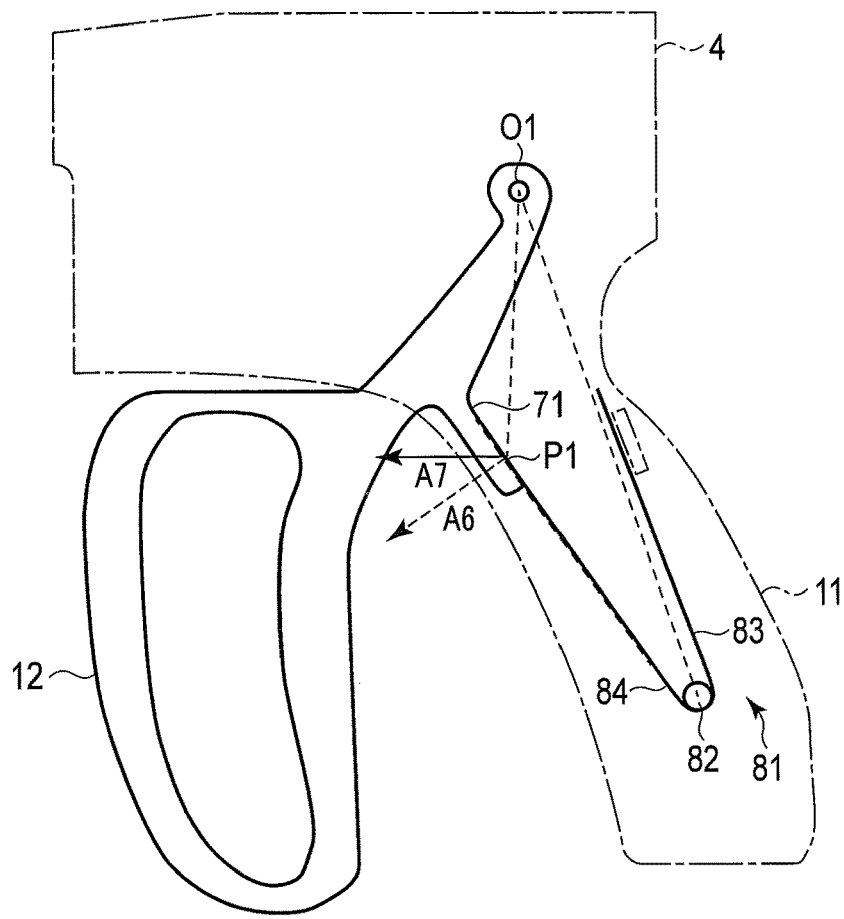
FIG. 12 is a view for explaining a configuration example of the spring provided in the handle.

A configuration example of a return spring that presses the handle 12 toward the distal side will be described with reference to FIG. 11 and FIG. 12. As shown in FIG. 11 and FIG. 12, the housing 4 includes a return spring 81 for pressing the handle 12 toward the distal side. The return spring 81 generates force so that a first linear member 83 and a second linear member 84 are opened about an axis 82. Here, the first linear member 83 is fixed to the housing 4. On the other hand, the second linear member 84 pushes a spring support portion 71 of the handle 12 toward the distal side. When the handle 12 is pushed toward the proximal side by the user, the return spring 81 is compressed by this force. On the other hand, when the handle 12 is released from the force of the user, the return spring 81 pushes the handle 12 back to the distal side.

In the example shown in FIG. 11, the second linear member 84 is arranged on a line connecting the support axis O1 of the handle 12 and the axis 82 of the return spring 81. The force generated by the return spring 81 acts in the perpendicular direction of the second linear member 84 as indicated by an arrow A5, and this direction coincides with the rotational direction of the handle 12. Therefore, the force of the return spring effectively acts on the handle 12.

On the other hand, in the example shown in FIG. 12, the second linear member 84 is not arranged on a line connecting the support axis O1 of the handle 12 and the axis 82 of the return spring 81. As a result, of the force generated by the return spring indicated by an arrow A6, the force used for rotation of the handle 12 becomes a component indicated by an arrow A7. That is, the force of the return spring does not efficiently act on the handle 12. Therefore, the arrangement as shown in FIG. 11 is preferable to the arrangement as shown in FIG. 12.

[Regarding First Grasping Piece]

Figure 13:
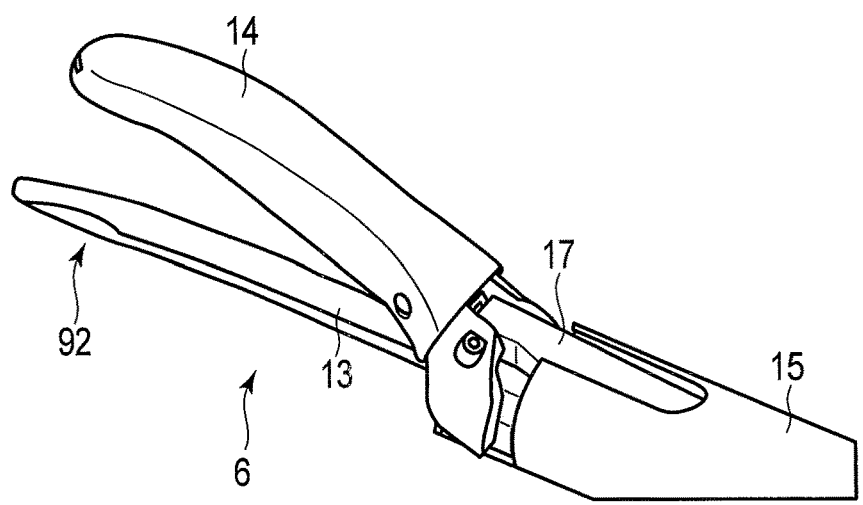
FIG. 13 is a perspective view schematically showing a configuration example of a first grasping piece having a depressed portion.

FIG. 13 shows an example of the shape of the first grasping piece 13 of the end effector. The first grasping piece 13 is formed to be thin so as to be easily inserted into a narrow space. Furthermore, in the example shown in FIG. 13, the side surface of the first grasping piece 13 may be provided with a depressed portion 92. The depressed portion 92 gives a spoon-like shape to the first grasping piece 13. The user can perform an operation of removing the living tissue to be treated, utilizing the depressed portion 92 like a spoon provided in the first grasping piece 13.

Figure 16:
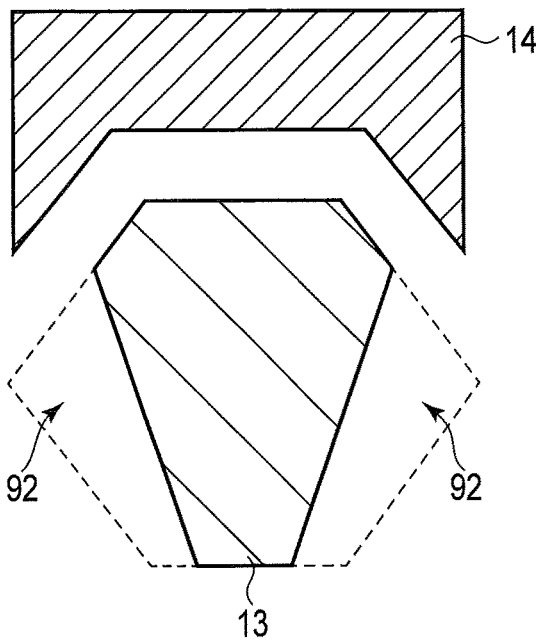
FIG. 16 is a schematic cross-sectional view for explaining an example of a position of the depressed portion provided in the first grasping piece.

The depressed portion 92 is provided in a direction different from the vertical direction in which the second grasping piece 14 is opened/closed. The position where the depressed portion 92 is provided will be described with reference to FIG. 14 to FIG. 16 that show schematic views of the cross section perpendicular to the longitudinal axis of the first grasping piece 13 and the second grasping piece 14. As shown in FIG. 14, the direction in which the depressed portion 92 is provided may be a right-left direction of the first grasping piece 13. As shown in FIG. 15 and FIG. 16, the direction in which the depressed portion 92 is provided may be a diagonally lower right-left direction of the first grasping piece 13. Note that the depressed portions 92 do not have to be on both right and left sides of the first grasping piece 13, and may be only on the right or left side.

As described above, the depressed portion 92 is provided, for example, not on the lower side or the like of the first grasping piece 13, but on the right or left side of the first grasping piece 13, and therefore the second grasping piece 14 is less likely brought into contact with the treatment target. Therefore, the second grasping piece 14 hardly hinders the operation. As a result, the user can easily perform the operation of removing the living tissue by using the first grasping piece 13 like a spatula.

Figure 17:
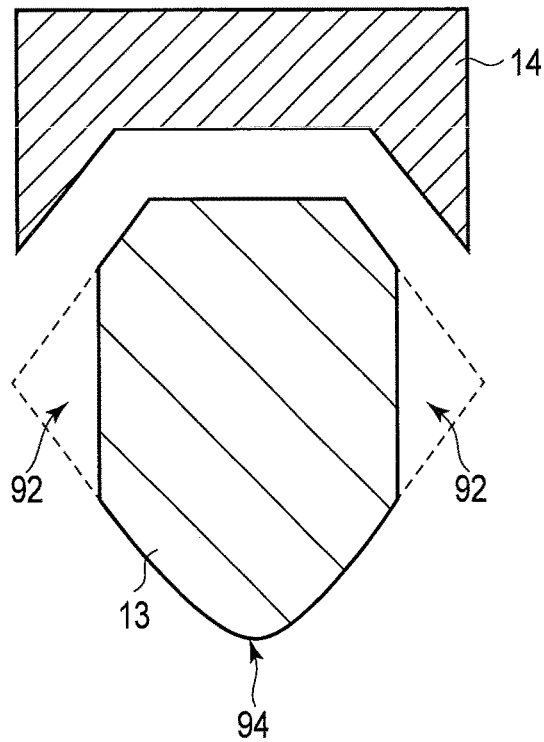
FIG. 17 is a schematic cross-sectional view for explaining an example of a shape of the first grasping piece.

When the depressed portion 92 is utilized, since the first grasping piece 13 is moved right and left on the living tissue, the lower surface of the first grasping piece 13 that is brought into contact with the living tissue may be a curved surface 94 as shown in FIG. 17. With such a shape, the first grasping piece 13 can be easily moved right and left. This is not limited to when the depressed portion 92 is utilized, and is also suitable when the end effector 6 is moved right and left in order to perform treatment on a wide surface.

Figure 18:
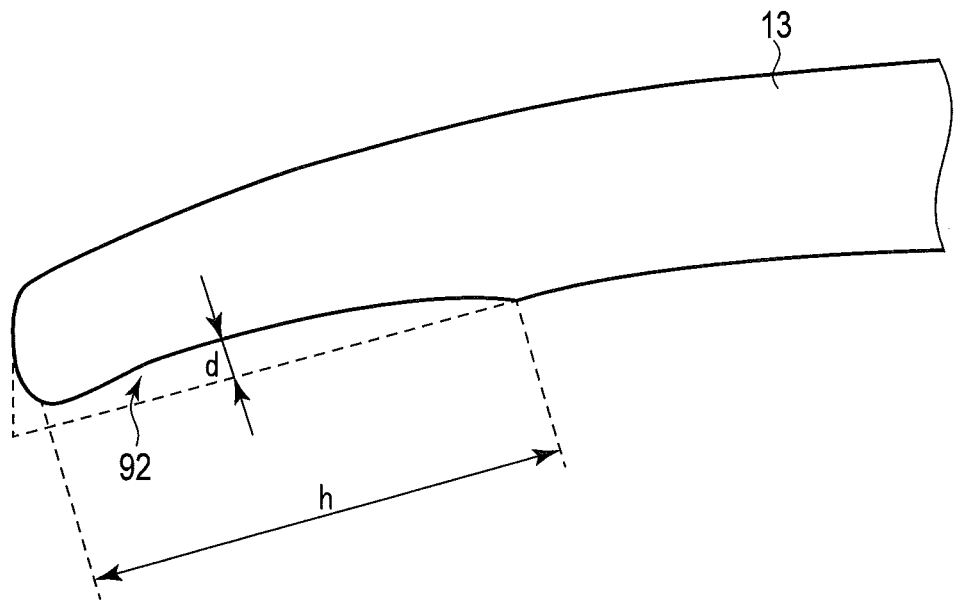
FIG. 18 is a view for explaining an example of a shape of the depressed portion provided in the first grasping piece.
Figure 19:
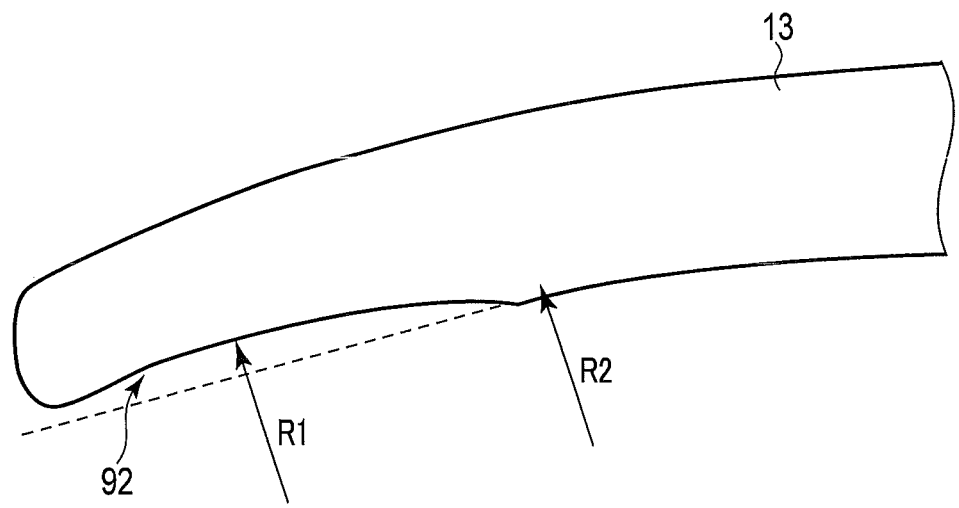
FIG. 19 is a view for explaining an example of a shape of the depressed portion provided in the first grasping piece.

The shape of the depressed portion 92 preferable for performing the operation of removing the living tissue will be described with reference to FIG. 18 and FIG. 19. FIG. 18 and FIG. 19 show the first grasping piece 13 viewed from the upper side.

As shown in FIG. 18, a depth d of the depressed portion 92 viewed from the upper direction is shorter than a length h of the depressed portion 92. In particular, the ratio between the depth d and the length h is preferably about d:h=1:10.

Furthermore, as shown in FIG. 19, a curvature R1 of the portion where the depressed portion 92 is formed as viewed from the upper direction is smaller than a curvature R2 of the slightly curved first grasping piece 13. In particular, the ratio between the curvature R1 of the depressed portion 92 and the curvature R2 of the first grasping piece 13 is preferably about R1:R2=1:5.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment instrument comprising:
   a sheath;
   a first grasping piece provided at a distal end of the sheath;
   a second grasping piece connected to the sheath to rotate about a first rotation axis perpendicular to a longitudinal axis of the sheath so as to be opened and closed with respect to the first grasping piece;
   a movable member connected to the second grasping piece, and configured to move along the longitudinal axis; and
   a second rotation axis connecting the second grasping piece and the movable member, provided in parallel with the first rotation axis, and configured to convert movement of the movable member along the longitudinal axis into movement of the second grasping piece in an opening/closing direction, wherein the first rotation axis is rotatable and movable in the opening/closing direction with respect to at least one of the sheath and the second grasping piece, and the second rotation axis is rotatable and movable in the opening/closing direction with respect to at least one of the movable member and the second grasping piece, wherein:
one of the second grasping piece and the movable member is provided with a second axis member that forms the second rotation axis, and another of the second grasping piece and the movable member is provided with a second groove or hole that holds the second axis member; and
the second groove or hole is formed to be larger than an outer diameter of the second axis member such that the second axis member can rotate and move within a plane perpendicular to the second rotation axis.

2. The grasping treatment instrument according to claim 1, wherein:
a direction in which the second grasping piece is opened and closed is defined as a vertical direction; and
the second groove or hole has a first length in the vertical direction that is longer than a second length in a direction along the longitudinal axis.

3. The grasping treatment instrument according to claim 1, wherein an outer edge of the second groove or hole is closed.

4. The grasping treatment instrument according to claim 1, wherein one of the second grasping piece and the sheath is provided with a first axis member that forms the first rotation axis, and another of the second grasping piece and the sheath is provided with a first groove or hole that holds the first axis member.

5. The grasping treatment instrument according to claim 4, wherein the first groove or hole is formed to be larger than an outer diameter of the first axis member.

6. The grasping treatment instrument according to claim 5, wherein:
a direction in which the second grasping piece is opened and closed is defined as a vertical direction; and
the first groove or hole has a first length in the vertical direction that is longer than a second length in a direction along the longitudinal axis.

7. The grasping treatment instrument according to claim 5, wherein an outer edge of the first groove or hole includes an opening.

8. The grasping treatment instrument according to claim 1, wherein when a state in which the second grasping piece is most opened with respect to the first grasping piece is defined as an open state, and a state in which the second grasping piece is most closed with respect to the first grasping piece is defined as a closed state, in a process of transition from the open state to the closed state, the first rotation axis does not move within the sheath and the second grasping piece in a process of transition from a predetermined state to the closed state.

9. The grasping treatment instrument according to claim 1, wherein the second rotation axis is configured to move within at least one of the movable member and the second grasping piece in a plane perpendicular to the second rotation axis and in a direction intersecting with the longitudinal axis.

10. The grasping treatment instrument according to claim 1, wherein the first rotation axis and the second rotation axis are provided on sides opposite to each other with a center axis of the sheath therebetween.

11. The grasping treatment instrument according to claim 10, wherein the movable member passes through the sheath, and a distal end portion of the movable member protrudes from the sheath, and is curved on a side opposite to the first rotation axis.

12. The grasping treatment instrument according to claim 1, wherein the second rotation axis is fixed to the second grasping piece, and configured to move within the movable member, and when a state in which the second grasping piece is most opened with respect to the first grasping piece is defined as an open state, and a state in which the second grasping piece is most closed with respect to the first grasping piece is defined as a closed state, a locus of the second rotation axis depicted on the movable member in a process of transition from the open state to the closed state is such that a perpendicular line to a tangent of the locus always coincides with a perpendicular line to a line connecting the first rotation axis and the second rotation axis in the process of transition.

13. A method of assembling a grasping treatment instrument, the grasping treatment instrument comprising:
a sheath;
a first grasping piece provided at a distal end of the sheath;
a second grasping piece connected to the sheath to rotate about a first rotation axis perpendicular to a longitudinal axis of the sheath so as to be opened and closed with respect to the first grasping piece;
a movable member connected to the second grasping piece, and configured to move along the longitudinal axis;
a second rotation axis connecting the second grasping piece and the movable member, provided in parallel with the first rotation axis, and configured to convert movement of the movable member along the longitudinal axis into movement of the second grasping piece in an opening/closing direction;
a first axis member provided on one of the second grasping piece and the sheath;
a first groove or hole provided on another of the second grasping piece and the sheath, having an inner diameter larger than an outer diameter of the first axis member, comprising an opening provided on an outer edge of the first groove of hole, and holding the first axis member;
a second axis member provided on one of the second grasping piece and the movable member; and
a second groove or hole provided on another of the second grasping piece and the movable member, having an inner diameter larger than an outer diameter of the second axis member, and holding the second axis member, wherein:
one of the second grasping piece and the movable member is provided with a second axis member that forms the second rotation axis, and another of the second grasping piece and the movable member is provided with a second groove or hole that holds the second axis member; and
the second groove or hole is formed to be larger than an outer diameter of the second axis member such that the second axis member can rotate and move within a plane perpendicular to the second rotation axis;
the method comprising:
connecting the second grasping piece and the sheath by inserting the first axis member from the opening of the outer edge of the first groove or hole and fitting the first axis member to the first groove or hole to form the first rotation axis; and connecting the first grasping piece and the movable member by connecting the second axis member and the second groove or hole to form the second rotation axis.

14. A method of disassembling a grasping treatment instrument, the grasping treatment instrument comprising:
a sheath;
a first grasping piece provided at a distal end of the sheath;
a second grasping piece connected to the sheath to rotate about a first rotation axis perpendicular to a longitudinal axis of the sheath so as to be opened and closed with respect to the first grasping piece; a movable member connected to the second grasping piece, and configured to move along the longitudinal axis; and
a second rotation axis connecting the second grasping piece and the movable member, provided in parallel with the first rotation axis, and configured to convert movement of the movable member along the longitudinal axis into movement of the second grasping piece in an opening/closing direction, the second grasping piece and the sheath comprising:
  a first axis member provided on one of the second grasping piece and the sheath; and
  a first groove or hole provided on another of the second grasping piece and the sheath, having an inner diameter larger than an outer diameter of the first axis member, comprising an opening on an outer edge, and holding the first axis member, the second grasping piece and the sheath being connected by engaging the first axis member and the first groove or hole, and the second grasping piece and the movable member comprising:
  a second axis member provided on one of the second grasping piece and the movable member; and
  a second groove or hole provided on an other of the second grasping piece and the movable member, each having an inner dimeter larger than an outer diameter of the second axis member, and holding the second axis member, the second grasping piece and the movable member being connected by connecting the second axis member and the second groove or hole, wherein:
    one of the second grasping piece and the movable member is provided with a second axis member that forms the second rotation axis, and another of the second grasping piece and the movable member is provided with a second groove or hole that holds the second axis member; and
    the second groove or hole is formed to be larger than an outer diameter of the second axis member such that the second axis member can rotate and move within a plane perpendicular to the second rotation axis the method comprising:
releasing connection between the second axis member and the second groove or hole in the second rotation axis; and
releasing connection between the first axis member and the first groove or hole by moving the first axis member to be removed from the opening in the first rotation axis.

* * * * *